United States Patent
Sakai et al.

(10) Patent No.: US 7,970,101 B2
(45) Date of Patent: Jun. 28, 2011

(54) X-RAY ANALYZER AND X-RAY ANALYSIS METHOD

(75) Inventors: Noriaki Sakai, Chiba (JP); Toshiyuki Takahara, Chiba (JP); Yoshiki Matoba, Chiba (JP)

(73) Assignee: SII Nanotechnology Inc. (JP)

( * ) Notice: Subject to any disclaimer, the term of this patent is extended or adjusted under 35 U.S.C. 154(b) by 104 days.

(21) Appl. No.: 12/544,562

(22) Filed: Aug. 20, 2009

(65) Prior Publication Data

US 2010/0046700 A1 Feb. 25, 2010

(30) Foreign Application Priority Data

Aug. 22, 2008 (JP) ................................. 2008-214715
Oct. 29, 2008 (JP) ................................. 2008-277732

(51) Int. Cl.
*G01N 23/223* (2006.01)
*G01N 23/203* (2006.01)
(52) U.S. Cl. ................. 378/46; 378/44; 378/45; 378/88
(58) Field of Classification Search .................... 378/44, 378/45, 46, 48, 49, 50, 88, 89, 90
See application file for complete search history.

(56) References Cited

U.S. PATENT DOCUMENTS

| 6,038,280 A | * | 3/2000 | Rossiger et al. ................ 378/50 |
| 6,324,251 B1 | * | 11/2001 | Kuwabara ........................ 378/48 |
| 6,345,086 B1 | * | 2/2002 | Ferrandino et al. ............. 378/44 |
| 6,647,090 B2 | * | 11/2003 | Kawahara et al. .............. 378/45 |
| 6,885,726 B2 | * | 4/2005 | Uehara et al. ................... 378/44 |
| 7,313,220 B2 | * | 12/2007 | Katz ................................ 378/44 |
| 2001/0021240 A1 | * | 9/2001 | Kojima et al. .................. 378/45 |

FOREIGN PATENT DOCUMENTS

JP 04-175648 A 6/1992

* cited by examiner

*Primary Examiner* — Allen C. Ho
(74) *Attorney, Agent, or Firm* — Brinks Hofer Gilson & Lione

(57) ABSTRACT

An X-ray tube which irradiates a primary X-ray to an irradiation point on a sample, an X-ray detector which detects a characteristic X-ray and a scattered X-ray emitted from the sample and outputs a signal including energy information on the characteristic X-ray and scattered X-ray, an analyzer which analyzes the signal, a sample stage on which the sample is placed, a moving mechanism which moves the sample on the sample stage, the X-ray tube, and the X-ray detector relative to each other, a height measuring mechanism which measures a maximum height of the sample, and a control unit which adjusts the distance between the sample and the X-ray tube and the distance between the sample and the X-ray detector by controlling the moving mechanism on the basis of the measured maximum height of the sample, are included.

8 Claims, 6 Drawing Sheets

US 7,970,101 B2

X-RAY ANALYZER AND X-RAY ANALYSIS METHOD

RELATED APPLICATIONS

This application claims priority under 35 U.S.C. §119 to Japanese Patent Application Nos. JP2008-214715 filed on Aug. 22, 2008 and JP2008-277732 filed on Oct. 29, 2008, the entire contents of which are hereby incorporated by reference.

BACKGROUND OF THE INVENTION

1. Field of the Invention

The present invention relates to an X-ray analyzer and an X-ray analysis method suitable for X-ray mapping analysis of a sample surface using fluorescent X-ray analysis and the like.

2. Description of the Related Art

In the fluorescent X-ray analysis, an X-ray emitted from an X-ray source is irradiated onto a sample, a fluorescent X-ray which is a characteristic X-ray emitted from the sample is detected by an X-ray detector, and a spectrum is acquired from the energy and a qualitative analysis or quantitative analysis of the sample is performed. Fluorescent X-ray analysis is widely used in process management, quality management, and the like since a sample is quickly analyzed without being broken. In recent years, as measurement of small amounts has become possible due to improvements in precision and sensitivity, fluorescent X-ray analysis is expected to be widely used particularly as an analysis method of detecting harmful substances included in materials, composite electronic components, and the like.

In the related art, for example, in JP-A-04-175648 (Claims, FIG. 3), a fluorescent X-ray analyzer including a sample stage on which a sample is placed, an X-ray tube which irradiates an X-ray, an X-ray detector which detects a fluorescent X-ray generated from the sample by the X-ray irradiation, a pulse processor which determines an element included in the sample and the intensity on the basis of an output of the X-ray detector, a computer to which a signal from the pulse processor is input, an image processing device which performs image processing by processing an output of the computer, and a stage controller which moves the sample stage in a predetermined direction on the basis of a control signal from the computer, is disclosed.

The following problems remain in the known technique described above.

That is, when performing fluorescent X-ray analysis, it is necessary to bring the X-ray source and X-ray detector as close as possible to a sample in order to analyze the sample with good sensitivity. However, as shown in FIG. 4, in the case of an uneven sample S like a mounting board or in the case of a sample having a thin pin shaped or thin line shaped protruding portion (for example, a thin metal wire based on wire bonding) which is difficult to be viewed by an observation system, such as an image processing device, or by visual observation, there has been a possibility that an X-ray tube 2 or an X-ray detector 3 is brought too close to the sample S on a sample stage 1 at the time of X-ray irradiation distance adjustment and as a result, the X-ray tube 2 or the X-ray detector 3 may collide with the sample S accidentally.

SUMMARY OF THE INVENTION

In view of the above, it is an object of the invention to provide an X-ray analyzer and an X-ray analysis method capable of avoiding collision of an apparatus and a sample even when the sample is uneven.

The invention adopts the following configuration in order to solve the above-described problems. That is, according to an aspect of the invention, an X-ray analyzer includes: a radiation source which irradiates a radial ray to an irradiation point on a sample; an X-ray detector which detects a characteristic X-ray and a scattered X-ray emitted from the sample and outputs a signal including energy information on the characteristic X-ray and scattered X-ray; an analyzer which analyzes the signal; a sample stage on which the sample is placed; a moving mechanism which moves the sample on the sample stage, the radiation source, and the X-ray detector relative to each other; a height measuring mechanism which measures the maximum height of the sample; and a control unit which adjusts the distance between the sample and the radiation source and the distance between the sample and the X-ray detector by controlling the moving mechanism on the basis of the measured maximum height of the sample.

In addition, according to another aspect of the invention, an X-ray analysis method of irradiating a radial ray from a radiation source to an irradiation point on a sample, detecting a characteristic X-ray and a scattered X-ray emitted from the sample and outputting a signal including energy information on the characteristic X-ray and scattered X-ray by an X-ray detector, and analyzing the signal by an analyzer includes: measuring a maximum height of the sample by a height measuring mechanism; and determining a position of the irradiation point by moving the sample on a sample stage, the radiation source, and the X-ray detector relative to each other by a moving mechanism. In the determining of the position of the irradiation point, a control unit adjusts the distance between the sample and the radiation source and the distance between the sample and the X-ray detector by controlling the moving mechanism on the basis of the measured maximum height of the sample.

That is, in the X-ray analyzer and the X-ray analysis method, since the control unit adjusts the distance between the sample and the radiation source and the distance between the sample and the X-ray detector by controlling the moving mechanism on the basis of the measured maximum height of the sample, collision of the sample and the apparatus can be avoided by comparing the height positions of the radiation source and X-ray detector with the maximum height of the sample and restricting the range of movement (for example, a height-direction movable range of the sample stage) made by the moving mechanism such that the radiation source and the X-ray detector are positioned above the maximum height position of the sample.

Moreover, in the X-ray analyzer according to the aspect of the invention, it is preferable to further include a distance measuring unit which measures the distance between the irradiation point and the radiation source and the distance between the irradiation point and the X-ray detector. In addition, preferably, the control unit disposes the radiation source and the X-ray detector above the maximum height of the sample using the moving mechanism when the height of the irradiation point is lower than the maximum height of the sample, and corrects a parameter which is used in calculation for quantitative analysis according to the difference between the standard irradiation position of a radial ray and the height position of the irradiation point measured by the distance measuring unit when performing the calculation on the basis of data analyzed by the analyzer.

Moreover, in the X-ray analysis method according to the aspect of the invention, it is preferable to further include: disposing the radiation source and the X-ray detector above the maximum height of the sample using the moving mechanism when the height of the irradiation point is lower than the maximum height of the sample; and measuring the distance between the irradiation point and the radiation source and the distance between the irradiation point and the X-ray detector by a distance measuring unit after determining the position of the irradiation point, wherein the control unit corrects a parameter which is used in calculation for quantitative analysis according to the difference between the standard irradiation position of a radial ray and the height position of the irradiation point when performing the calculation on the basis of data acquired by the analyzer.

Since the height-direction movable range of the sample stage on which the sample is placed is restricted, the standard irradiation position of a radial ray and the height position of an actual irradiation point are shifted from each other according to the uneven shape of the sample which influences an analysis value. However, in the X-ray analyzer and the X-ray analysis method according to the aspects of the invention, when performing calculation for quantitative analysis on the basis of data acquired by the analyzer, the parameter used in the calculation is corrected according to the difference between the standard irradiation position of a radial ray and the height position of the irradiation point. Accordingly, a correct analysis result can be obtained with no influence from the amount of change in distance.

Moreover, in the X-ray analyzer according to the aspect of the invention, preferably, the height measuring mechanism has a function of calculating the maximum height of the sample on the basis of the amount of blocked light or light blocking position when the laser light is blocked by the sample or the amount of reflected light when the laser light is reflected by the sample by changing the positional relationship between the sample and laser light relative to each other while irradiating the laser light onto the sample. That is, in the X-ray analyzer, the maximum height of the sample is calculated on the basis of the amount of blocked light or light blocking position when the laser light is blocked by the sample or the amount of reflected light when the laser light is reflected by the sample by changing the positional relationship between the sample and laser light relative to each other while irradiating the laser light onto the sample. Accordingly, the maximum height of the sample can be correctly measured in a non-contact way.

Moreover, in the X-ray analyzer according to the aspect of the invention, it is preferable that the height measuring mechanism be provided to measure the maximum height of the sample in a state where the sample is placed on the sample stage. That is, in the X-ray analyzer, since the height measuring mechanism is provided so as to be able to measure the maximum height of the sample in a state where the sample is placed on the sample stage, the sample on the sample stage can be directly measured immediately before analysis. Accordingly, compared with a case where the maximum height of the sample is measured before the sample is placed on the sample stage, the distance between the sample and the radiation source and the distance between the sample and the X-ray detector at the time of analysis can be calculated more correctly.

Moreover, in the X-ray analyzer according to the aspect of the invention, preferably, the sample is built in a housing formed of a material allowing the radial ray to be transmitted therethrough, and the height measuring mechanism measures a maximum height of the housing as the maximum height of the sample.

Moreover, in the X-ray analysis method according to the aspect of the invention, preferably, the sample is built in a housing formed of a material allowing the radial ray to be transmitted therethrough, and the maximum height of the housing is measured as the maximum height of the sample in the measuring of the maximum height.

In the X-ray analyzer and the X-ray analysis method, the distance between the sample in the housing and the radiation source and the distance between the sample in the housing and the X-ray detector can be appropriately adjusted while avoiding collision of the housing and the apparatus by measuring the maximum height of the housing as the maximum height of the sample built in the housing formed of a material allowing the radial ray to be transmitted therethrough. Accordingly, the inside sample can be analyzed in a state where the sample is covered with the housing.

According to the invention, the following effects are obtained.

That is, in the X-ray analyzer and the X-ray analysis method according to the aspects of the invention, the control unit adjusts the distance between the sample and the radiation source and the distance between the sample and the X-ray detector by controlling the moving mechanism on the basis of the measured maximum height of the sample. This restricts the range of movement made by the moving mechanism so that collision of the sample and the apparatus can be avoided. Accordingly, optimization of analysis performance according to an uneven state of a sample can be realized by acquiring information on the height of the sample.

As a result, an operator can safely perform the measurement without being concerned about collision.

DETAILED DESCRIPTION OF THE PREFERRED EMBODIMENTS

Figure 1:
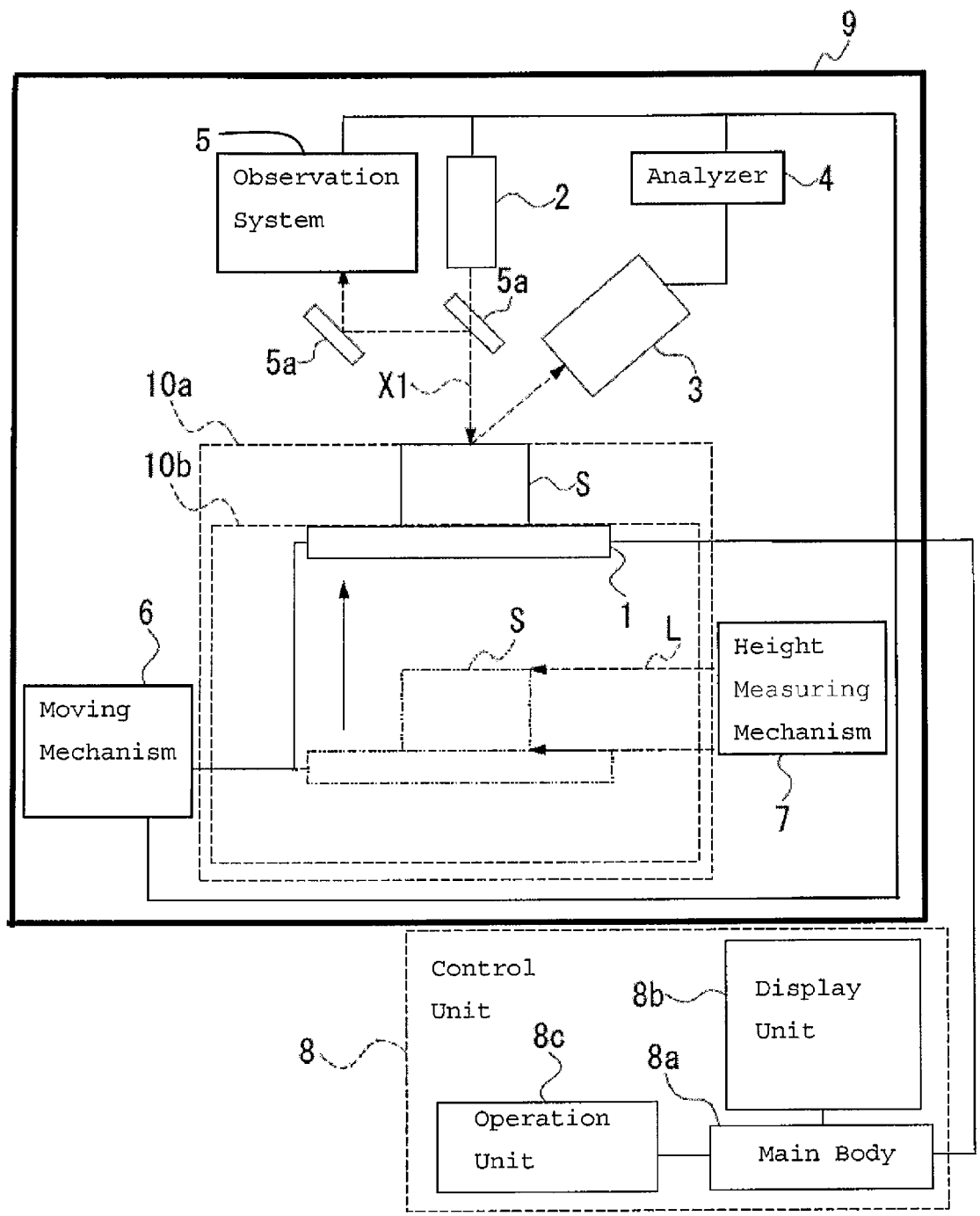
FIG. 1 is a view schematically illustrating the entire configuration of an X-ray analyzer in an embodiment of X-ray analyzer and X-ray analysis method according to the invention.

Hereinafter, an embodiment of X-ray analyzer and X-ray analysis method according to the invention will be described with reference to FIGS. 1 to 3. Incidentally, in each drawing used for the following description, the scale of each member may be suitably adjusted in order to have a recognizable size as is required.

The X-ray analyzer of the present embodiment is an energy dispersive fluorescent X-ray analyzer, for example. As shown in FIGS. 1 and 2, the X-ray analyzer of the present embodiment includes: a sample stage (moving mechanism) 1 on which a sample S is placed and which is movable; an X-ray tube (radiation source) 2 which irradiates a primary X-ray (radial ray) X1 to an arbitrary irradiation point P1 on the sample S; an X-ray detector 3 which detects a characteristic X-ray and a scattered X-ray emitted from the sample S and outputs a signal including energy information on the characteristic X-ray and scattered X-ray; an analyzer 4 which is connected to the X-ray detector 3 and analyzes the above signal; an observation system 5 having an optical microscope or the like which acquires, as image data, an image of the sample S illuminated by an illumination unit (not shown); a moving mechanism 6 which can move the sample S on the sample stage 1, the X-ray tube 2, and the X-ray detector 3 relative to each other; a height measuring mechanism 7 which can measure the maximum height of the sample S; and a control unit 8 which is connected to the analyzer 4 and performs analysis processing for determining the X-ray intensity corresponding to a specific element.

The X-ray tube 2 emits an X-ray, which is generated when a thermal electron generated from a filament (cathode) in the tube is accelerated by a voltage applied between the filament (cathode) and a target (anode) and collides with W (tungsten), Mo (molybdenum), Cr (chromium), and the like of the target, as the primary X-ray X1 through a window, such as a beryllium foil.

The X-ray detector 3 includes a semiconductor detection element (not shown; for example, an Si (silicon) element which is a pin-structure diode) provided at an X-ray incidence window. When one X-ray photon is incident, the X-ray detector 3 generates a current pulse corresponding to the one X-ray photon. An instantaneous current value of the current pulse is proportional to the energy of the incident characteristic X-ray. In addition, the X-ray detector 3 is set to convert the current pulse generated in the semiconductor detection element into a voltage pulse, and amplify and output the voltage pulse as a signal.

The analyzer 4 is a pulse height analyzer (multi-channel analyzer) which obtains the pulse height of a voltage pulse from the signal and generates an energy spectrum.

The observation system 5 is configured to include an optical microscope, a camera for observation, and the like by which an enlarged image and the like of the sample S can be viewed and imaged through a plurality of mirrors 5a provided. In addition, at least some mirrors 5a are of a movable type, such that the mirrors 5a can move back from the course of the primary X-ray X1 at the time of analysis. In addition, the observation system 5 has a focusing adjustment mechanism.

The sample stage 1 is an XYZ stage which can move vertically and horizontally and whose height can be adjusted in a state where the sample S is fixed thereon.

In addition, the moving mechanism 6 is configured to include a stepping motor which is connected to the sample stage 1 or is provided in the sample stage 1 in order to move the sample stage 1 vertically and horizontally.

The control unit 8 is a computer which is configured to include a CPU and the like and functions as an analysis processing device. The control unit 8 includes: a main body 8a of the control unit which determines the X-ray intensity corresponding to a specific element from the energy spectrum transmitted from the analyzer 4; a display unit 8b which displays an analysis result on the basis of the X-ray intensity; and an operation unit 8c which can input various commands, such as position input of the irradiation point P1, analysis conditions, and the like.

The height measuring mechanism 7 is set so as to be able to measure the maximum height of the sample S in a state where the sample S is placed on the sample stage 1. For example, an area sensor which is provided beside the sample stage 1 and which calculates the maximum height of the sample S on the basis of the amount of reflected light when the laser light L is reflected from the sample S by changing the positional relationship between the sample S and the laser light L relative to each other by the moving mechanism 6 while irradiating laser light L onto the sample S is adopted as the height measuring mechanism 7. That is, the height measuring mechanism 7 includes: a laser light source (not shown), such as a semiconductor laser, capable of horizontally emitting the belt-like laser light L which spreads out in a constant width in a vertical direction with respect to the mounting surface of the sample stage 1; and a light receiving unit (not shown) which receives the laser light L which is reflected and returns from the sample S on the sample stage 1.

In addition, the control unit 8 is set to adjust the distance between the sample S and the X-ray tube 2 and the distance between the sample S and the X-ray detector 3 by controlling the moving mechanism 6 on the basis of the measured maximum height of the sample S.

Figure 2:
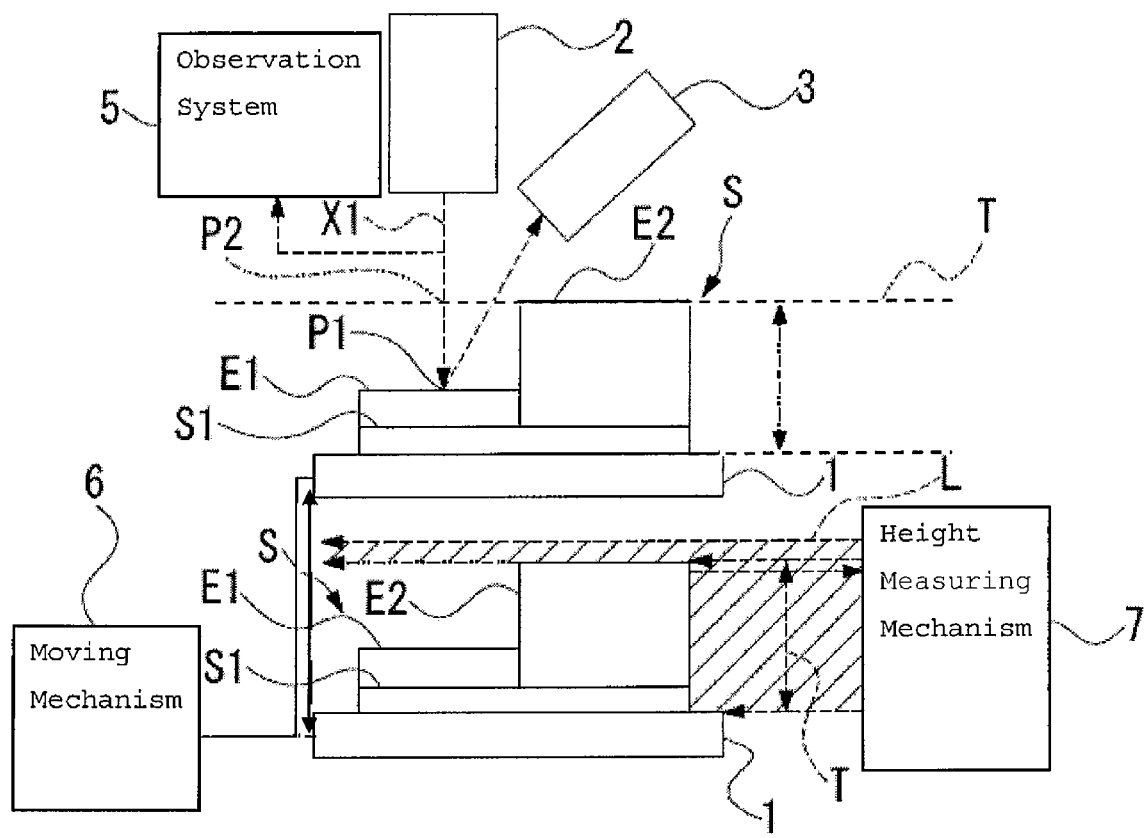
FIG. 2 is an explanatory view illustrating a method of measuring the maximum height of a sample by a height measuring mechanism in the present embodiment.

Moreover, as shown in FIG. 2, the control unit 8 controls the X-ray tube 2 and the X-ray detector 3 to be disposed above the maximum height of the sample S by using the moving mechanism 6 when the height of the irradiation point P1 is lower than the maximum height of the sample S.

In addition, the observation system 5 also functions as a distance measuring unit that calculates the distance between the irradiation point P1 on the sample S and the X-ray tube 2 by adjusting the focus of an optical microscope, a camera for observation, and the like of the observation system 5 for an image of the sample S illuminated by the illumination unit (not shown).

In addition, the control unit 8 is set to calculate the difference between a height position, which is calculated from the distance acquired by the observation system 5 which is a distance measuring unit, and a standard irradiation position, which is the distance from the X-ray tube 2 to a point where the irradiation axis of the primary X-ray X1 from the X-ray tube 2 and the direction (of the best sensitivity) of the X-ray detector 3 cross each other, and to correct parameters, such as an X-ray irradiation distance, used for quantitative calculation in the control unit 8 according to the difference.

Incidentally, in the present embodiment, the observation system 5 indirectly calculates the distance between the irradiation point P1 and the X-ray tube 2 by adjusting the focus. However, the distance between the irradiation point P1 and the X-ray detector 3 may be calculated.

The sample stage 1, the X-ray tube 2, the X-ray detector 3, the observation system 5, the height measuring mechanism 7, and the like are housed in a sample chamber 9 which can be decompressed. At the time of measurement, the sample chamber 9 is decompressed so that X-rays are not absorbed into the air.

Next, an X-ray analysis method using the X-ray analyzer of the present embodiment will be described with reference to FIGS. 1 and 2. Incidentally, for example, a sample in which a plurality of electronic components E1 and E2 with different heights are mounted on a mounting board S1 is used as the sample S.

First, the sample S is set on the sample stage 1, and then a maximum height T of the sample S is measured by the height measuring mechanism 7 within the sample chamber 9 as shown in FIG. 2. That is, the sample stage 1 is made to move up to the height, at which the mounting surface height position of the sample stage 1 matches the lower end of the belt-like laser light L, in a state where the vertically belt-like laser light L is emitted from the laser light source of the height measuring mechanism 7. Then, the sample stage 1 is horizontally moved to the laser light L by the moving mechanism 6.

In this case, when the laser light L is emitted to the electronic components E1 and E2 of the sample S, a part of the belt-like laser light L is blocked by the electronic components E1 and E2 and the laser light L corresponding to the amount of light blocked is reflected. In the light receiving unit of the height measuring mechanism 7, the reflected laser light L is received and an output change of the light receiving unit at this time is stored. After performing the measurement over the entire surface of the sample S, the maximum height T of the sample S is calculated from the lowest output value on the basis of the relationship between the output change of the light receiving unit and the height of the sample S stored beforehand.

In addition, the height measuring mechanism 7 outputs the measured maximum height T of the sample S to the control unit 8 and the control unit 8 stores the measured maximum height T. Incidentally, storage of the output change of the light receiving unit and calculation processing for calculating the maximum height T of the sample S from the lowest output value may be performed in the control unit 8, and not in the height measuring mechanism 7.

Then, the sample chamber 9 is made to have a predetermined decompressed state. Moreover, in order to perform fluorescent X-ray analysis, the control unit 8 drives the sample stage 1 using the moving mechanism 6 so that the sample S is moved and disposed immediately below the X-ray tube 2 and performs irradiation distance adjustment of the primary X-ray X1 so that the irradiation point P1 is placed at the irradiation position of the primary X-ray X1 emitted from the X-ray tube 2.

In this case, when determining the position of the irradiation point P1, the control unit 8 adjusts the distance between the sample S and the X-ray tube 2 and the distance between the sample S and the X-ray detector 3 by controlling the moving mechanism 6 on the basis of the measured maximum height T of the sample S. That is, when the height (height of the standard irradiation position of the primary X-ray X1) of the irradiation point P1 is lower than the maximum height T of the sample S, the control unit 8 moves the sample stage 1 using the moving mechanism 6 so that the X-ray tube 2 and the X-ray detector 3 are disposed above the maximum height T of the sample S. In addition, in FIG. 1, reference numeral 10a denotes an original movable range of the sample stage 1, and reference numeral 10b denotes a restricted movable range of the sample stage 1.

A characteristic X-ray and a scattered X-ray generated by irradiating the primary X-ray X1 from the X-ray tube 2 onto the sample S in a state where the position of the sample S and the positions of the X-ray tube 2 and X-ray detector 3 are set not to be in contact with each other as described above are detected by the X-ray detector 3.

The X-ray detector 3 which detected the X-rays transmits the signal to the analyzer 4, and the analyzer 4 acquires an energy spectrum from the signal and outputs it to the control unit 8.

The control unit 8 determines the X-ray intensity corresponding to a specific element from the energy spectrum transmitted from the analyzer 4 and displays the analysis result on the display unit 8b.

In this case, since the height-direction movable range of the sample stage 1 on which the sample S is placed is restricted as shown in FIG. 2, the optimal irradiation position (standard irradiation position P2 of the primary X-ray X1) of the primary X-ray X1 and the height position of the actual irradiation point P1 are shifted from each other according to the uneven shape of the sample S, which influences the analysis value. For this reason, in the present embodiment, the control unit 8 performs calculation after correcting the parameter, which is used in the calculation for quantitative analysis in the control unit 8, on the basis of data of the pulse height of the energy spectrum calculated by the analyzer 4 according to the difference between the standard irradiation position P2 of the primary X-ray X1 and the height position of the irradiation point P1.

In this case, the distance of the irradiation point P1 from the X-ray tube 2, the distance of the X-ray detector 3 from the irradiation point P1, the angle formed by the direction of the X-ray detector 3 and the irradiation point P1, and the like are applied as parameters for correction (hereinafter, referred to as correction parameters).

The reason is as follows. When there is a difference between the standard irradiation position P2 and the height position of the irradiation point P1, the energy density or irradiation region of the primary X-ray X1 irradiated onto the sample S is changed since the distance of the irradiation point P1 from the X-ray tube 2, the distance of the X-ray detector 3 from the irradiation point P1, the direction of the X-ray detector 3, the irradiation point P1, and the like are changed. Then, the intensity and the like of a fluorescent X-ray or scattered X-ray emitted from the sample S is changed or the intensity of the fluorescent X-ray or scattered X-ray detected by the X-ray detector 3 is changed. Accordingly, in this case, a quantitative analysis can be correctly performed by executing a calculation by adding correction parameters.

Furthermore, in the present embodiment, the angle formed by the direction of the X-ray tube 2 and the irradiation point P1 is not changed since the optical axis of the observation system 5 and the optical axis of the X-ray tube 2 are the same axes in the difference from the height position due to using the mirror 5a. However, in a configuration where the mirror 5a is not used, the optical axis of the observation system 5 and the optical axis of the X-ray tube 2 are different. In this case, therefore, a correction parameter of the angle formed by the direction of the X-ray tube 2 and the irradiation point P1 may be used.

Thus, in the X-ray analyzer and the X-ray analysis method of the present embodiment, the control unit 8 adjusts the distance between the sample S and the X-ray tube 2 and the distance between the sample S and the X-ray detector 3 by controlling the moving mechanism 6 on the basis of the measured maximum height T of the sample S. Accordingly, collision of the sample S and the apparatus can be avoided by comparing the height positions of the X-ray tube 2 and X-ray detector 3 with the maximum height T of the sample S and restricting the height-direction movable range of the sample stage 1 moved by the moving mechanism 6 such that the X-ray tube 2 and the X-ray detector 3 are positioned above the maximum height position of the sample S.

Furthermore, when the control unit 8 performs calculation for quantitative analysis according to the difference between the standard irradiation position P2 of the primary X-ray X1 and the height position of the irradiation point P1, a parameter used for the calculation is corrected according to the difference between the standard irradiation position P2 and the height position of the irradiation point P1. Accordingly, a correct analysis result can be obtained with no influence corresponding to the amount of change in distance.

Furthermore, since the height measuring mechanism 7 calculates the maximum height T of the sample S on the basis of the amount of reflected light when the laser light L is reflected from the sample S by changing the positional relationship between the sample S and the laser light L relative to each other while irradiating the laser light L onto the sample S, the maximum height T of the sample S can be correctly measured in a non-contact way.

Furthermore, since the height measuring mechanism 7 is provided to be able to measure the maximum height T of the sample S in a state where the sample S is placed on the sample stage 1, the sample S on the sample stage 1 can be directly measured immediately before analysis. Accordingly, compared with a case where the maximum height T of the sample S is measured before the sample S is placed on the sample stage 1, the distance between the sample S and the X-ray tube 2 and the distance between the sample S and the X-ray detector 3 at the time of analysis can be calculated more correctly.

Next, a method of analyzing a sample built in a housing using the X-ray analyzer of the present embodiment will be described with reference to FIGS. 5, 6A, and 6B.

Figure 5:
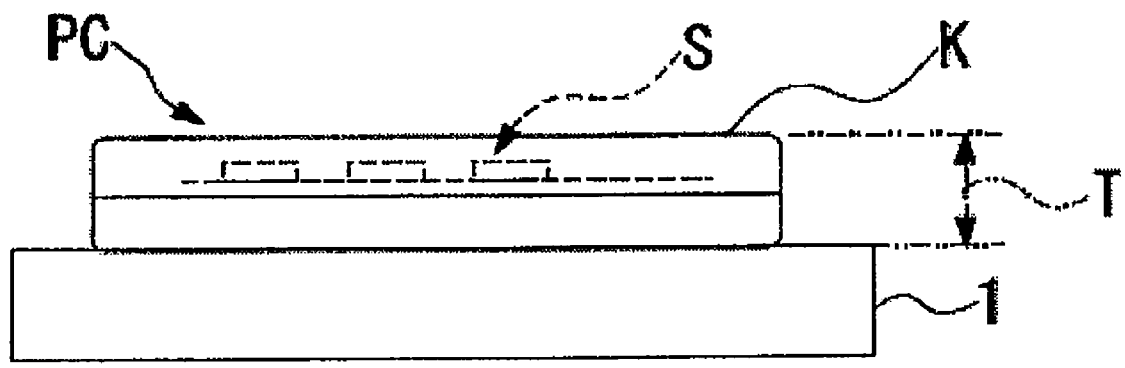
FIG. 5 is a view illustrating measurement of the maximum height when analyzing a sample built in a housing in the present embodiment.
Figure 6A:
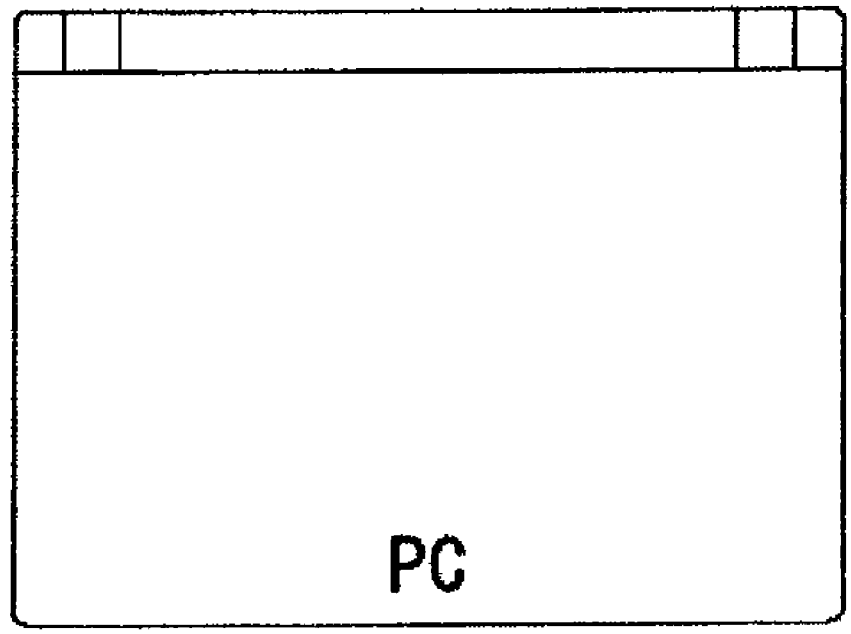
FIGS. 6A and 6B are schematic views illustrating a camera image and an inside analysis image of a notebook type personal computer as an example of when analyzing a sample built in a housing in the present embodiment.
Figure 6B:
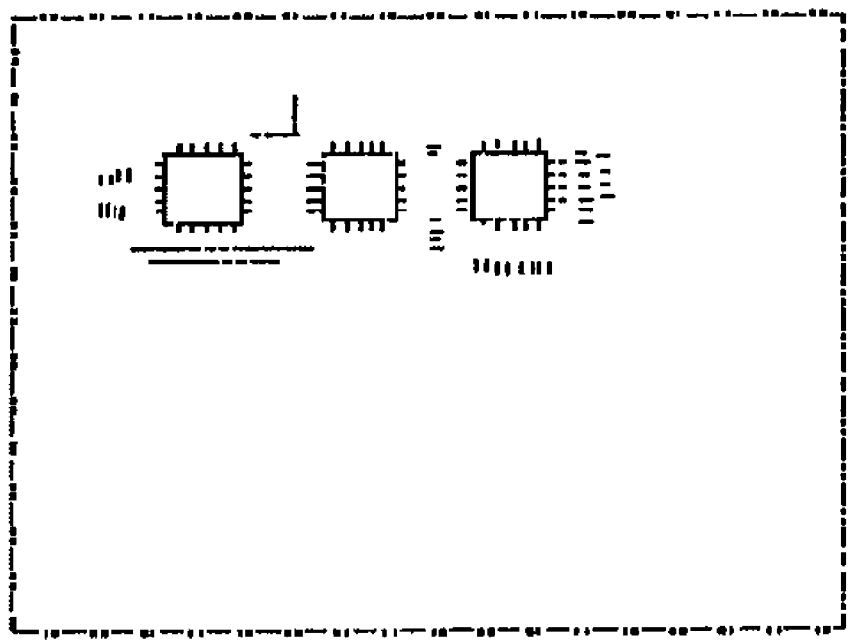

In this analysis method, as shown in FIGS. 5 and 6A, for example, a circuit board built in a housing K of a notebook type personal computer PC as an electronic apparatus is analyzed as the sample S.

In the case of performing the analysis, the height measuring mechanism 7 measures the maximum height T of the housing K in a state where the notebook type personal computer PC is placed on the sample stage 1 as shown in FIG. 5 and sets the value as the maximum height of the sample S, and the control unit 8 adjusts the distance between the sample S and the X-ray tube 2 and the distance between the sample S and the X-ray detector 3 by controlling the moving mechanism 6 on the basis of the measured maximum height T of the housing K.

An existing electronic apparatus, such as a notebook type personal computer PC, is covered with the housing K formed of an exterior material, such as plastic or thin aluminum. Accordingly, even if elemental analysis of the sample S, such as an inside circuit board, is performed in a state where the electronic apparatus is covered with the housing K, X-rays from the target element are absorbed into the housing K. As a result, the intensity becomes very weak. For this reason, even if mapping of the analysis result is tried, it takes a very long time to perform measurement, which was not practically effective.

In the present embodiment, however, the distance between the sample S in the housing K and the X-ray tube 2 and the distance between the sample S in the housing K and the X-ray detector 3 can be appropriately adjusted while avoiding collision of the housing K and the apparatus by measuring the maximum height T of the housing K as the maximum height of the sample S built in the housing K formed of a material allowing the primary X-ray to be transmitted therethrough. Accordingly, mapping analysis of the inside sample S can be performed qualitatively in a state where the sample S is covered with the housing K as shown in FIG. 6B.

That is, by appropriately adjusting the distance between the inside sample S and the X-ray tube 2 and the distance between the inside sample S and the X-ray detector 3 in consideration of the height of the housing K, setting to the position (normally, most adjacent position in many cases) at which the intensity of X-rays from the sample S is sufficiently large can be performed. As a result, elemental analysis of the sample S, such as an inside circuit board, becomes possible in a state where the sample S is covered with the housing K. For example, according to this analysis method, for a camera image of the notebook type personal computer PC shown in FIG. 6A, an analysis image, such as lead (Pb) in the inside sample S, can be obtained as shown in FIG. 6B.

Thus, when inspecting the existence of a harmful element in an electronic apparatus, the existence of a harmful element in the electronic apparatus can be screened without disassembling the electronic apparatus. As a result, the labor involved in inspection can be significantly reduced.

Moreover, for example, the shape of an inside substrate may be acquired as an analysis image by changing the element to be detected to one with a high X-ray energy.

It should be understood that the technical scope of the invention is not limited to the above embodiment, but various modifications may be made without departing from the spirit and scope of the invention.

Figure 3:
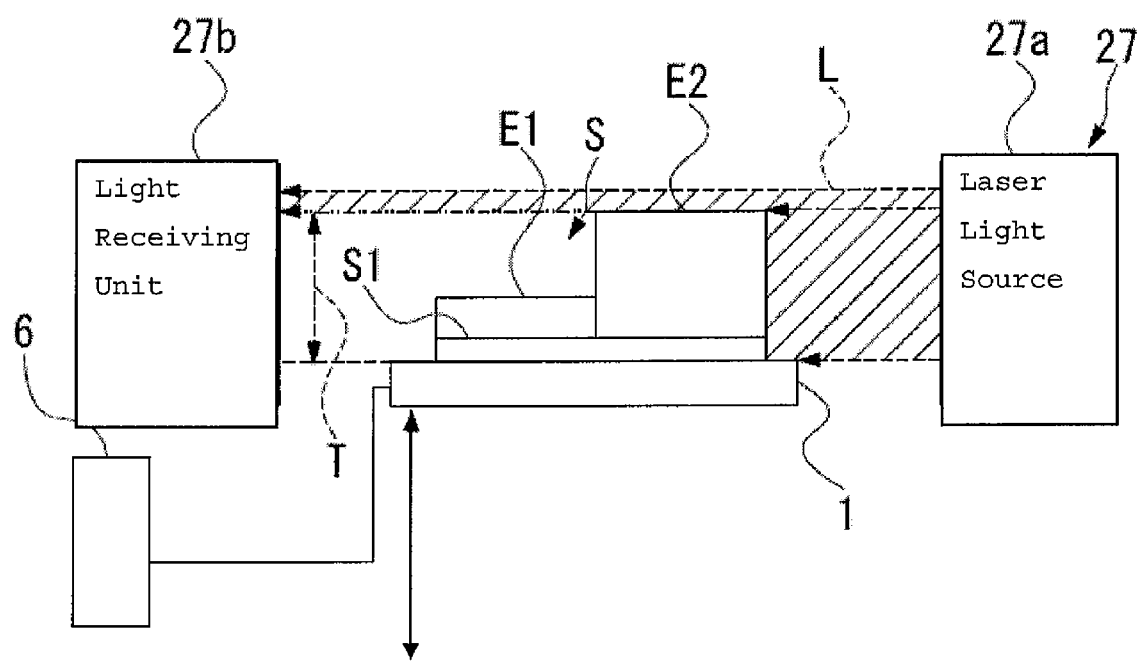
FIG. 3 is an explanatory view illustrating a method of measuring the maximum height of a sample by another height measuring mechanism in the present embodiment.
Figure 4:
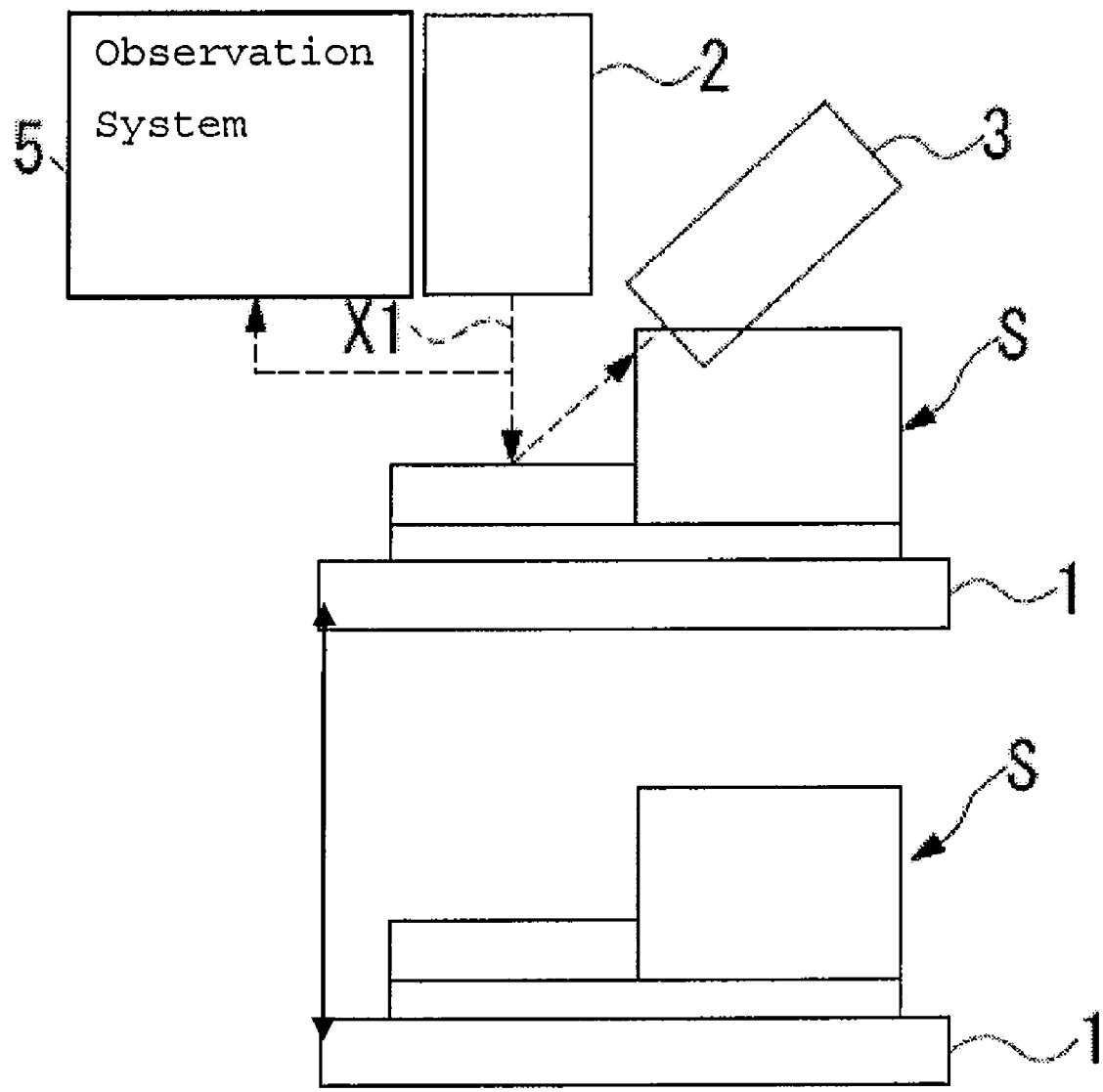
FIG. 4 is an explanatory view illustrating the positional relationships between a sample and an X-ray tube and between the sample and an X-ray detector at the time of analysis in a known example of the X-ray analyzer and X-ray analysis method according to the invention.

For example, although the area sensor, which calculates the maximum height of a sample on the basis of the amount of reflected light when laser light is reflected from the sample and which includes a light emitting unit and a light receiving unit, is adopted as the height measuring mechanism in the above-described embodiment, a height measuring mechanism 27 which calculates the maximum height of a sample on the basis of the amount of blocked light when laser light is blocked by the sample may also be adopted as another example as shown in FIG. 3. The height measuring mechanism 27 includes: a laser light source 27a, such as a semiconductor laser, which is provided at one side of the sample stage 1, for example, and which can horizontally emit the belt-like laser light L which spreads out in a constant width in a vertical direction with respect to the mounting surface of the sample stage 1; and a light receiving unit 27b which is provided at the other side of the sample stage 1 so as to be opposite to the laser light source 27a and which can receive the laser light L.

In a state where the laser light L is horizontally emitted from the laser light source 27a of the height measuring mechanism 27 and is then received in the light receiving unit 27b, the sample stage 1 is horizontally moved by the moving mechanism 6. In this case, when the electronic component E2 which is the highest of the entire surface of the sample S blocks the laser light L, the amount of received light of the laser light L in the light receiving unit 27b is most reduced. The reduced amount of received light is equivalent to the amount of blocked light when the laser light L is blocked by the sample S. After performing the measurement over the entire surface of the sample S, the maximum height T of the sample S is calculated from the lowest output value on the basis of the relationship between the output change of the light receiving unit 27b and the height of the sample S stored beforehand.

Moreover, in the above-described embodiment, the maximum height of a sample is measured by moving the sample placed on the sample stage in one direction of the horizontal direction with respect to the belt-like laser light using the height measuring mechanism. However, it is also possible to perform similar measurement twice by changing the moving direction of the sample to horizontal directions of two directions perpendicular to each other with respect to the laser light, to acquire height data of the sample in a two-dimensional way, and to set a highest portion in the two-dimensional measurement range as a maximum height. In this case, the region which has a maximum height in a two-dimensional way can be specified. Accordingly, even if there is a high region in one local area, there is no need of separating the X-ray tube and the X-ray detector from the sample uselessly in a portion where the X-ray tube or the X-ray detector and the sample do not interfere with each other excluding the high region. As a result, it becomes possible to obtain a much better sensitivity.

Although the vertically belt-like laser light is emitted in the above-described height measuring mechanism, it is also possible to emit belt-like laser light which spreads out in a constant width in a horizontal direction and to move a sample stage up and down with respect to laser light using a moving mechanism. Also in this case, since a sample on the sample stage that is moved up and down blocks or reflects the belt-like laser light, the output in the light receiving unit changes. Accordingly, the maximum height of the sample can be calculated from the output change and the vertical position of the sample.

Moreover, in the above-described height measuring mechanism, the maximum height of the sample is measured by measuring the amount of blocked light or the amount of reflected light, which is the relative light amount change when the laser light is blocked by the sample, in the light receiving unit. However, it is also possible to adopt a method of calculating the maximum height of a sample at the light blocking position when laser light is blocked by the sample. For example, by providing a CCD type light receiving unit, in which a plurality of light receiving elements is arrayed at least in the height direction, at a position opposite a laser light source and detecting a sensing state of laser light for every element of the CCD type light receiving unit, it is possible to detect the maximum height of a sample by outputting the highest position coordinates of the element by which the laser light is blocked.

As the height measuring mechanism, a laser type height measuring mechanism capable of performing measurement in a non-contact way as described above is preferable. However, a contact sensing type sensor may also be adopted as long as there is no influence on the sample.

In addition, as described above, it is preferable to provide the height measuring mechanism inside the sample chamber and to measure the maximum height of a sample in a state where the sample is placed on the sample stage. However, it is also possible to provide the height measuring mechanism inside a load lock chamber which transports a sample and to measure the maximum height of the sample during the transport, for example.

In addition, although the analysis is performed in a condition where the sample chamber is decompressed in the above-described embodiment, the analysis may also be performed in a condition where the sample chamber is not in a vacuum (decompressed) state.

In addition, although the invention is applied to the energy dispersive fluorescent X-ray analyzer in the above-described embodiment, the invention may also be applied to X-ray analyzers using other analysis methods, for example, a wavelength dispersive fluorescent X-ray analyzer and an SEM-EDS (scanning electron microscope and energy dispersive X-ray analysis) apparatus which uses an electron ray as a radial ray irradiated and can also obtain a secondary electron image.

What is claimed is:

1. An X-ray analyzer comprising:
   a radiation source which irradiates a radial ray to an irradiation point on a sample;
   an X-ray detector which detects a characteristic X-ray and a scattered X-ray emitted from the sample and outputs a signal including energy information on the characteristic X-ray and scattered X-ray;
   an analyzer which analyzes the signal;
   a sample stage on which the sample is placed;
   a moving mechanism which moves the sample on the sample stage, the radiation source, and the X-ray detector relative to each other;
   a height measuring mechanism which measures a maximum height of the sample; and
   a control unit which adjusts a distance between the sample and the radiation source and a distance between the sample and the X-ray detector by controlling the moving mechanism on the basis of the measured maximum height of the sample.

2. The X-ray analyzer according to claim 1, further comprising:
   a distance measuring unit which measures the distance between the irradiation point and the radiation source and the distance between the irradiation point and the X-ray detector,
   wherein the control unit disposes the radiation source and the X-ray detector above the maximum height of the sample using the moving mechanism when the height of the irradiation point is lower than the maximum height of the sample, and corrects a parameter which is used in calculation for quantitative analysis according to a difference between a standard irradiation position of a radial ray and a height position of the irradiation point measured by the distance measuring unit when performing the calculation on the basis of data analyzed by the analyzer.

3. The X-ray analyzer according to claim 1,
   wherein the height measuring mechanism comprises a laser light source that emits a laser light and has a function of calculating the maximum height of the sample on the basis of the amount of blocked light or light blocking position when the laser light is blocked by the sample or the amount of reflected light when the laser light is reflected by the sample by changing the positional relationship between the sample and laser light relative to each other while irradiating the laser light onto the sample.

4. The X-ray analyzer according to claim 1,
   wherein the height measuring mechanism is provided to measure the maximum height of the sample in a state where the sample is placed on the sample stage.

5. The X-ray analyzer according to claim 1,
   wherein the sample is built in a housing formed of a material allowing the radial ray to be transmitted therethrough, and
   the height measuring mechanism measures a maximum height of the housing as the maximum height of the sample.

6. An X-ray analysis method of irradiating a radial ray from a radiation source to an irradiation point on a sample, detecting a characteristic X-ray and a scattered X-ray emitted from the sample and outputting a signal including energy information on the characteristic X-ray and scattered X-ray by an X-ray detector, and analyzing the signal by an analyzer, the method comprising:
   measuring a maximum height of the sample by a height measuring mechanism; and
   determining a position of an irradiation point by moving the sample on a sample stage, the radiation source, and the X-ray detector relative to each other by a moving mechanism,
   wherein determining the position of the irradiation point comprises adjusting a distance between the sample and the radiation source and a distance between the sample and the X-ray detector by controlling the moving mechanism on the basis of the measured maximum height of the sample.

7. The X-ray analysis method according to claim 6, further comprising:
disposing the radiation source and the X-ray detector above the maximum height of the sample by the control unit using the moving mechanism when the height of the irradiation point is lower than the maximum height of the sample; and
measuring the distance between the irradiation point and the radiation source and the distance between the irradiation point and the X-ray detector by a distance measuring unit after determining the position of the irradiation point,
wherein the control unit corrects a parameter which is used in calculation for quantitative analysis according to a difference between a standard irradiation position of a radial ray and a height position of the irradiation point when performing the calculation on the basis of data acquired by the analyzer.

8. The X-ray analysis method according to claim 6,
wherein the sample is built in a housing formed of a material allowing the radial ray to be transmitted therethrough, and
the maximum height of the housing is measured as the maximum height of the sample in the measuring of the maximum height.

* * * * *